United States Patent [19]

Shorr et al.

[11] Patent Number: 5,055,517

[45] Date of Patent: Oct. 8, 1991

[54] ELECTROPHORETIC MEDIA

[75] Inventors: Robert Shorr, Overbrook Hills; Tikam Jain, King of Prussia, both of Pa.

[73] Assignee: AT Biochem, Malvern, Pa.

[21] Appl. No.: 331,222

[22] Filed: Mar. 31, 1989

Related U.S. Application Data

[63] Continuation-in-part of Ser. No. 188,467, Apr. 29, 1988, abandoned.

[51] Int. Cl.$^5$ ............................................. C08K 33/00
[52] U.S. Cl. ..................................... 524/813; 524/833; 524/845; 524/916; 524/423
[58] Field of Search ................ 524/813, 833, 845, 916

[56] References Cited

U.S. PATENT DOCUMENTS

| | | | |
|---|---|---|---|
| 4,243,507 | 1/1981 | Martin et al. | 204/301 |
| 4,388,428 | 6/1983 | Kuzma et al. | |
| 4,415,428 | 11/1983 | Nochumson et al. | 204/299 |
| 4,548,869 | 10/1985 | Ogawa et al. | 428/474.7 |
| 4,548,870 | 10/1985 | Ogawa et al. | 428/474.7 |
| 4,579,783 | 4/1986 | Ogawa et al. | 428/475.2 |
| 4,582,868 | 4/1986 | Ogawa et al. | 524/211 |
| 4,600,641 | 7/1986 | Ogawa et al. | 428/355 |
| 4,652,354 | 3/1987 | Place et al. | 204/182.8 |
| 4,654,132 | 3/1987 | Takagi et al. | 204/182.8 |
| 4,657,656 | 4/1987 | Ogawa | 252/315.1 |
| 4,695,354 | 9/1987 | Sugihara et al. | 204/180.1 |
| 4,699,705 | 10/1987 | Ogawa et al. | 204/299 |

OTHER PUBLICATIONS

Masson, Patrick et al., "Hydrophobic Interaction Electrophoresis Under High Hydrostatic Pressure Upon the Interaction of Serum Albumin with a Long-Chain Aliphatic Ligand," *Electrophoresis*, vol. 9, pp. 157–161 (1988).

*Primary Examiner*—Joseph L. Schofer
*Assistant Examiner*—Mark D. Sweet
*Attorney, Agent, or Firm*—Woodcock Washburn Kurtz Mackiewicz & Norris

[57] ABSTRACT

Electrophoretic media based on polymers with novel structures are disclosed. In one preferred embodiment, the polymers are formed by cross-linking polymerization of N,N-dimethylacrylamide with ethyleneglycol methacrylate. In another preferred embodiment, the polymers are formed by cross-linking polymerization of N,N-dimethylacrylamide and hydroxyethylmethacrylate with N,N-dimethylbisacrylamide.

15 Claims, 6 Drawing Sheets

FORMULA N

GUINEA PIG LEG MUSCLE CRUDE EXTRACT
SOYBEAN TRYPSIN INHIBITOR

D GRADIENT 7%−12%, .14%B, .28%H

ELECTROPHORETIC MEDIA

RELATED APPLICATIONS

This is a continuation-in-part of U.S. Pat. Ser. No. 188,467, filed Apr. 29, 1988 now abandoned.

BACKGROUND OF THE INVENTION

This invention relates to novel electrophoretic media. The media preferably comprise polymer gels which exhibit greater strength, resolution and recoverability of separated products such as DNA than commercially available gels. The media can also be otherwise formulated, such as in bead form and as a surface coating.

During the last decade, considerable advances have been made in molecular biology revolving around the ability to manipulate peptides, DNA and RNA. These advances have fueled the emergence of the biotechnology industry, with extensive research and development geared to the production of biopharmaceuticals, genetically engineered vaccines, immunochemicals, organisms, plants and novel diagnostics. Electrophoresis, a technique in which complex biological substances such as proteins, peptides, DNA and RNA are separated according to size and/or charge, is a powerful separation method widely used within every life science discipline. The procedure is used for the resolution and isolation of complex biological substances such as proteins, peptides, DNA and RNA, and is thus a technique upon which the emerging biotechnology industry is greatly dependent. The needs of the industry have placed new and increased demands on electrophoretic technology, there being a considerable need for electrophoretic media which can provide improved resolution, handleability, and recovery and a range of matrix pore sizes which can be used in newly discovered applications.

Most analytical electrophoresis methods are based on zone electrophoresis in which a thin zone of a sample is applied to the electrophoretic medium. When the components of the sample are to be separated according to their charge, an electric potential is applied to the electrophoretic medium for a certain period of time, so that charged components of the sample move in various distances depending on their chemical natures. When the components of the sample are to be separated according to their size, the electrophoretic medium contains a denaturing agent so that components of the sample move in various distances depending on their molecular weights. The migration of the sample components results in the formation of fractional zones which can then be examined and studied by application of standard electrophoretic practices such as fixing, staining, and washing to remove buffers. Typically, the electrophoretic medium is a thin gel slab supported by a suitable material, commonly glass or plastic.

Various hydrophilic colloids, such as starch, cellulose acetate and agarose have been used in the forming of electrophoretic gel slabs, but polyacrylamide is generally favored. Polyacrylamide is used as a cast material composed of varying amounts of acrylamide and bis-acrylamide. N,N$^1$-bisacrylylcystamine, N,N$^1$-dihydroxy ethylene bis-acrylamide, and N,N$^1$-diallyltartardiamide have also been used. These materials are conventionally proportioned to prepare, on polymerization, a network of polymeric fibers for sieving or anticorrection. Viscosity of the gel is adjusted by varying the amounts of acrylamide and bis-acrylamide. Frequently used catalyst and initiator are TEMED (tetraethylaminediamine) and ammonium persulfate or riboflavin/light.

Methods known in the art for utilizing polyacrylamide gels for determination of nucleotide sequences involve the preparation of the gels in given thicknesses, such as between glass plates to a thickness of approximately 0.3 mm. In some applications the gel may be polymerized onto a support film. DNA samples labeled such as with $^{32}$P, $^{35}$S or fluorescent dyes are placed onto sample slots and electrophoresed. After electrophoresis (1-24 hours) the gel is removed from the glass plates and autoradiography performed. In automated systems, fluorescent labeled nucleotides are monitored during the separation. Autoradiography requires 10 to 20 hours after which time films are studied to determine nucleotide sequence. The preparation of gels for autoradiography of $^{35}$S nucleotides requires immersion in 10% acetic acid to remove urea and handling of the gels with caution due to extreme fragility.

When proteins are being separated by electrophoretic methods based on their size, sodium dodecyl sulfate (SDS) is generally added to the polyacrylamide gel alone, or in conjunction with other denaturants, to unfold the protein and provide a net negative charge. Molecular sizes can be estimated from mobilities as compared to known standards. When separations are being made according to charge, the polyacrylamide gels are generally used in combination with acidic, basic or neutral buffer systems in the absence of denaturing agents. Electrodes are positioned according to the predicted net charge of the sample at the pH used.

Despite the widespread use of polyacrylamide gels to separate complex proteins, double or single stranded DNA, synthetic oligonucleotides and the like as well as for DNA sequencing, a number of disadvantages are associated with polyacrylamide. Among them are neurotoxicity, short shelf life, cumbersome preparation, and gel fragility. Neurotoxicity and instability have only recently been addressed in the development of adequate precast polyacrylamide gels. Gel fragility is considered a major difficulty in DNA sequencing where ultrathin gels are required for optimum resolution on autoradiography of radiolabeled nucleotides. These disadvantages are also found in other applications of electrophoresis such as separation of proteins.

Recognizing the shortcomings of polyacrylamide gels, many have attempted to improve the gels. U.S. Pat. No. 4,657,656 to Ogawa discloses an improved medium for electrophoresis comprising a polyacrylamide gel formed by crosslinking polymerization of an acrylamide compound and a crosslinking agent and further containing a water soluble polymer having a molecular weight in the range of 10,000 to 1,000,000, such as polyvinyl alcohol or polyacrylamide. Incorporation of the water soluble polymer such as solid polyacrylamide is said to reduce the brittleness of the polyacrylamide gel.

U.S. Pat. No. 4,695,354 to Sugihara et al. discloses that conventional thin polyacrylamide gels are unsuitable because, when used to resolve nucleic acid fragments, they give distorted patterns. Sugihara et al. disclose that the resolution of the gels can be improved by incorporating into the gels less than 1 wt/v % of glycerol.

The fragility and brittleness of conventional polyacrylamide gel membranes can lead to problems when it is desired to dry the membranes for enhanced resolution. As disclosed in U.S. Pat. No. 4,699,705 to Ogawa et al., in the drying process, the adhesion between the glass plate and the membrane is negligible, the membrane is easily broken. To alleviate these problems,

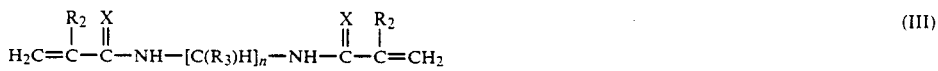

and

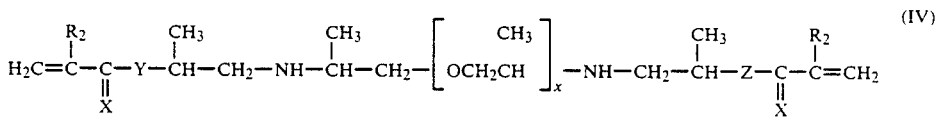

Ogawa et al. disclose that the adhesion between the membrane and its support can be enhanced by utilizing as the support a polymer sheet which has been subjected to glow discharge treatment. The patent also suggests the incorporation in the gel medium of at least one carbamoyl group-containing compound, such as urea or formamide, as modifier. Other methods disclosed for improving the adhesion between a polyacrylamide gel membrane and its support involve the use of special adhesives as disclosed in U.S. Pat. Nos. 4,548,869, 4,548,870, 4,579,783 and U.S. Pat. No. 4,600,641 to Ogawa et al. and in U.S. Pat. No. 4,415,428 to Nochumson et al.

U.S. Pat. No. 4,582,868 to Ogawa et al. notes that the polymerization reaction for the preparation of polyacrylamide can be inhibited by the presence of oxygen. It discloses a novel medium for electrophoresis in the form of an aqueous gel which can be prepared in the presence of oxygen. The novel medium is an acrylamide copolymer having a specifically selected repeating unit.

Despite the great amount of effort which has gone into improving conventional polyacrylamide gels, there is still a need for new gels which overcome the problems associated with acrylamide gels such as brittleness, neurotoxicity, cumbersome preparation and short shelf life. There is also a need for new gels which have greater resolution power and recoverability of separated DN and protein materials to meet the demands of the emerging biotechnology industry.

SUMMARY OF THE INVENTION

Electrophoretic media based on polymers with novel structures have now been found which provide improved resolution and overcome many of the disadvantages associated with conventional polyacrylamide and agarose gels. In one embodiment of this invention, the electrophoretic medium comprises an aqueous gel formed by crosslinking polymerization in the presence of aqueous medium and in the absence of oxygen of one or more monomers of the formula

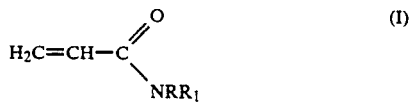

where
R=alkyl, optionally mono-substituted with

—OH or with —C(0)CH$_2$C(0)CH$_3$;
R$_1$=H or alkyl, optionally mono-substituted with—OH or with —C(0)CH$_2$C(0)CH$_3$; and
one or more cross-linking agents selected from compounds of the formula where
m=an integer of 2 or more;
n=an integer of 2 or more;
x=an integer from 1-20;
R$_2$=H, alkyl or halogen;
R$_3$=H, OH, NH$_2$, —SH, —SO$_2$OH, —PO$_4$$^{-3}$, or an alkyl, cycloalkyl, heterocyclic or aromatic moiety substituted with one or more groups selected from OH, NH$_2$, —SH, —SO$_2$OH, and —PO$_4$$^{-3}$;
X is selected from O and S;
and Y and Z are independently selected from —O— and —NH—.

These novel media utilize monomers which have been or are closely related to monomers suggested previously in the art, but utilize cross-linking agents substantially different from those previously suggested for polyacrylamide gels useful for the separation processes hereof. By virtue of the different cross-linking agents, the resulting gels have polymer structures different from those of conventional polyacrylamide gels and offer the advantages of greatly improved strength, greater resolution, greater recoverability of DNA samples and improved handling characteristics compared to the conventional gels.

In another embodiment of this invention, the electrophoretic medium comprises an aqueous gel formed by crosslinking polymerization in the presence of aqueous medium and in the absence of oxygen of one or more monomers of the formula

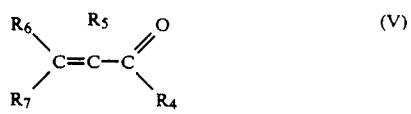

where
R$_4$=—OR$_8$, —SR$_8$ or —NR$_8$R$_9$;
R$_5$=H, halogen, or an alkyl, aromatic, cycloalkyl or heterocyclic group;
R$_6$ and R$_7$ are independently H or halogen;
R$_8$ and R$_9$ are independently H, a lipophilic unit or a hydrophilic moiety, provided that, when R$_4$=NR$_8$R$_9$, R$_8$ is other than H, alkyl or alkyl optionally mono-substituted with —OH or with—C(0)CH$_2$C(0)CH$_3$; and
one or more cross-linking agents selected from compounds of the formula

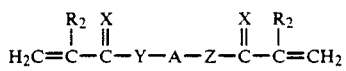

where $R_2$ is H or $CH_3$;

X is selected from O and S;

Y and Z are independently —O— or —NH—; and

A is a hydrophilic or lipophilic unit.

These novel polymers utilize monomers which have not, to the inventors' knowledge, been suggested previously in the art in combination with a wide variety of simple or complex cross-linking agents. Although difunctional cross-linking agents are discussed exclusively herein, it is believed that certain tri- or higher-functional agents may also be useful, and are deemed equivalent to the difunctional agents disclosed herein. By virtue of the different combinations of monomers and cross-linkers, the resulting gels have polymer structures chemically and architecturally different from those of conventional polyacrylamide gels, and tests indicate that they offer the advantages of greatly improved resolution, greater strength and thermal characteristics over the conventional gels.

In addition to the aforementioned electrophoretic media, this invention relates to the polymerization mixtures from which such media are prepared, i.e., the mixture of components such as monomers, cross-linking agents, catalysts, detergents and buffers which are used to prepare the electrophoretic media. This invention also relates to the novel polymers prepared by the cross-linking polymerization of the above-mentioned monomers and cross-linking agents. This invention also relates to beads formed by cross-linking polymerization of the above-mentioned monomers and cross-linking agents. Finally, this invention also relates to electrophoretic methods for effecting chromatographic separation of components in a chemical mixture using the above-mentioned electrophoretic media.

DETAILED DESCRIPTION OF THE DRAWINGS

DETAILED DESCRIPTION OF THE INVENTION

Figure 1:
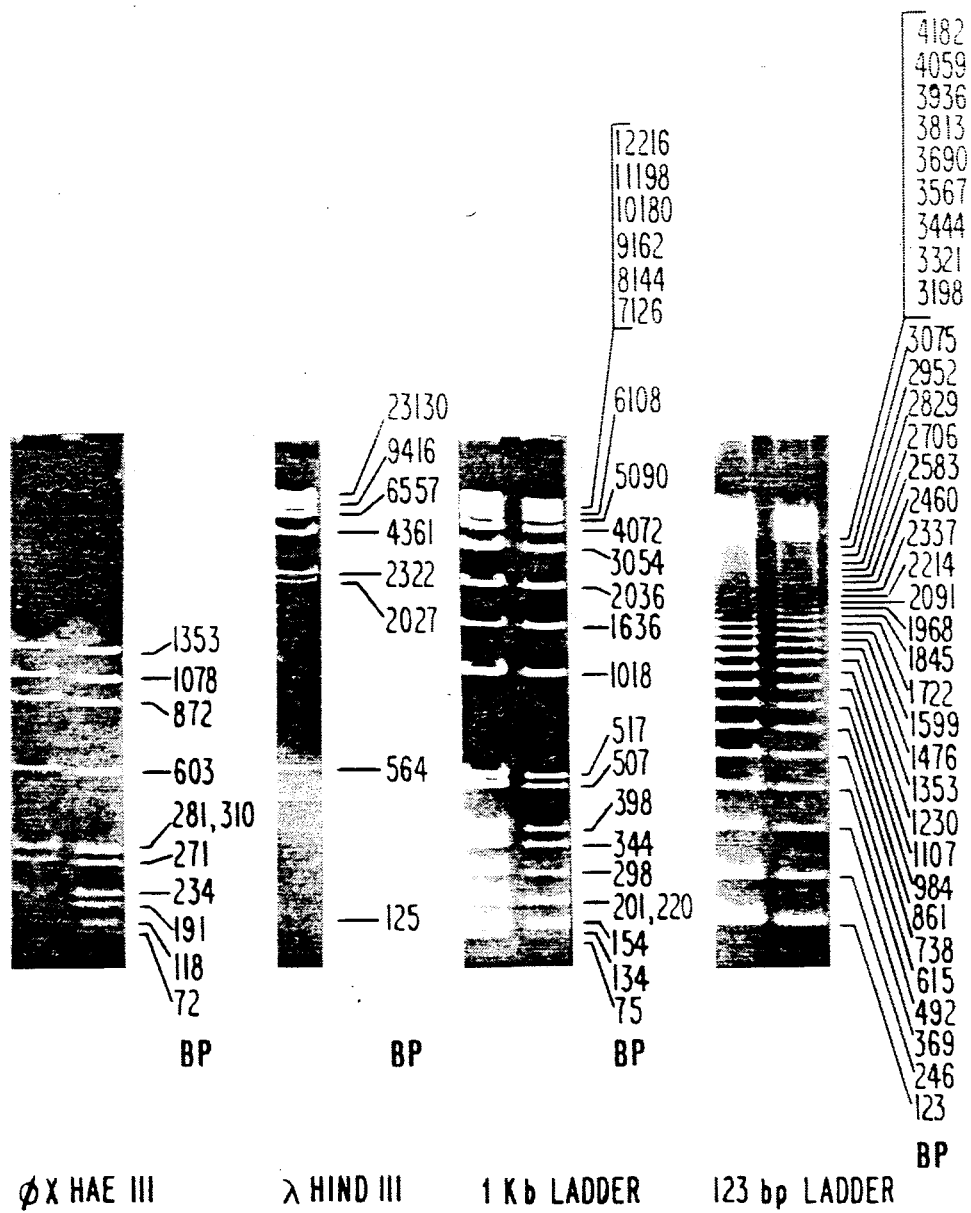
FIG. 1 shows an electrophoretic separation of DNA using the gel of Example 1.

The following terms are used herein to describe the electrophoretic media of this invention and, for the sake of clarity, may be defined as follows. "Alkyl" denotes a paraffinic hydrocarbon group, which may be straight-chained or branched, and which may be derived from an alkane by dropping one hydrogen from the formula. "Alkenyl" denotes an unsaturated hydrocarbon, straight-chained or branched, having at least one double bond. "Alkynyl" denotes an unsaturated hydrocarbon, straight-chained or branched, having at least one triple bond. "Cycloakyl" denotes an alkyl group having at least on ring. "Heterocyclic" denotes a structure having at least one saturated or unsaturated ring containing an atom selected from O, N and S. "Aromatic" denotes a cyclic hydrocarbon compound having one or more unsaturated rings. "Steroidal ring" denotes a polycyclic compound having as a nucleus a fused reduced 17-carbon-atom ring system, cyclopentanoperhydrophenanthrene. "Fatty acid" denotes a saturated or unsaturated carboxylic acid derived from or contained in an animal or vegetable fat or oil, having four to twenty-two carbon atoms and a terminal carboxyl radical. "Lipid chain" denotes esters of long-chain carboxylic acids. An "aliphatic polyol" is a straight-chained or branched alkyl, alkenyl or alkynyl group having at least two hydroxy substituents. An "alicyclic polyol" is a cyclic system substituted with at least two hydroxy substituents. A "simple sugar" is a molecule comprised of one saccharose group, e.g., glucose or fructose. An "amino sugar" is a carbohydrate carrying amino functions. "Hydrophilic" means having a strong affinity towards water. "Lipophilic" means having a strong affinity towards lipid-like molecules.

As indicated above, the novel gels and electrophoretic media of this invention have polymer structures significantly different from the structures of conventional polyacrylamide and agarose gels. In the first embodiment of this invention, acrylamide-type monomers previously suggested or similar to those suggested in the art are utilized in combination with new classes of cross-linking agents for use in electrophoresis. Preferably, in the monomers of Formula I, $R_1$ is other than H, and, more preferably, $R = R_1$. The most preferred monomer used in these gels is N,N-dimethylacrylamide, although other monomers of Formula I, such as but not limited to, N-methylacrylamide, N-propylacrylamide, N,N-dipropylacrylamide, N-isopropylamide, N,N-diisopropylamide, N-butylacrylamide, and N-methoxyacrylamide may be used. These monomers may be used alone or in combination with one another or in combination with monomers of Formula IV as described below.

In the preferred cross-linking agents, $R_2=H$, $R_3=OH$ and $X=O$. The cross-linking agents may be used alone or in combination with one another. Specific examples of suitable cross-linking agents of Formula II include the preferred ethyleneglycol dimethacrylate. Examples of suitable cross-linking agents of Formula IV include the preferred bisacrylate, bisacrylamido or acrylate/acrylamido derivatives of polymethylenehydroxyamines of the type sold under the tradename "Jeffamine" by Texaco Corporation. These derivatives ma be made by reacting the polymethylenehydroxyamine with two equivalents of acryloyl chloride or acrylic acid anhydride yielding the bisacrylate or bisacrylamide, or with one equivalent each of acryloyl chloride and acrylic acid anhydride yielding mixed acrylate/acrylamido analogs.

In the second embodiment of this invention, novel monomers of Formula V are utilized in combination with a broad spectrum of hydrophilic and lipophilic cross-linking agents. The monomers can be either esters ($R_4=-OR_8$), thioesters ($R_4=-SR_8$) or amides ($R_4 = -NR_8R_9$). The substitutions on the ester, thioester or amide functionality, $R_8$ and $R_9$, may be a lipophilic unit such as an alkyl group, an alkenyl group, an alkynyl group, a cycloalkyl group, a heterocyclic group, an aromatic group, a steroidal ring, a fatty acid chain or a lipid chain. Alternatively, the substitutions on the ester, thioester or amide functionality may be a hydrophilic group such as an aliphatic or alicyclic polyol, a simple or amino sugar, a thiosugar, a disaccharide, an aromatic or heterocyclic ring with polar substituents such as $-OH$, $-NH_2$, $-SH$, $-SO_2OH$ or $PO_4^{-3}$. Specific examples of suitable substitutions are presented in Table I.

TABLE I

| Hydrophilic Substituents | Lipophilic Substituents |
|---|---|
| $-(CH_2)_nOPO_3$, n = 1-3 | $-CH_2CH=CH_2$ |
| $-CH_2CH(OH)CH_2OH$ | $-CH_2C\equiv CH-CH_2-$ |
| $-CH_2CH(OH)CH_2OPO_3$ | $-CH_2-C_6H_5$ |
| $-NH_2-CHC(O)NHCH-COOH$ | $-C_6H_5$ |
| $-CH(OH)-CH(OH)-CH(OH)-CH_2OH$ | $-R-NH(CH_2)_3NH(CH_2)_4NH(CH_2)_3NH_2$ |
| $-C(CH_2OH)_3$ | |

(structures shown)

Examples of $R_5$ substituents are presented in Table II.

TABLE II

| $R_5$ Substituents |
|---|
| H |
| Cl |
| Br |
| I |
| F |
| $-(CH_2)_n-CH_3$, n = 0-10 |

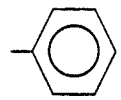

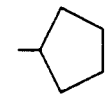

TABLE II-continued

R5 Substituents

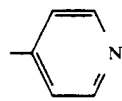

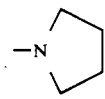

TABLE II-continued

R5 Substituents

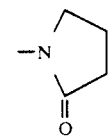

Examples of monomers within the scope of Formula V are presented below in Table III.

TABLE III

Monomers

[Structures shown:]

- piperidine-NH-C(O)-CH=CH$_2$
- piperazine-CH$_2$CH$_2$CH$_2$O-C(O)-CH=CH$_2$
- morpholine-NH-C(O)-CH=CH$_2$
- piperazine-C(O)-CH=CH$_2$
- 4-aminocyclohexyl-C(CH$_3$)$_2$-NH-C(O)-C(CH$_3$)=CH$_2$
- 4-(CH$_2$NHC(O)CH=CH$_2$)-piperidine
- adamantyl-NHC(O)CH=CH$_2$

- morpholine-CH$_2$CH$_2$CH$_2$NH-C(O)-C(CH$_3$)=CH$_2$
- morpholine-CH$_2$CH$_2$CH$_2$NH-C(O)-CH=CH$_2$
- piperazine-C(O)-C(CH$_3$)=CH$_2$
- $CH_2=C(CH_3)-C(O)-NHCH_2CH_2N(CH_2CH_3)_2$
- $CH_2=CH-C(O)-NHCH_2CH_2N(CH_2CH_3)_2$
- $CH_2=CH-C(O)-NHCH_2CH_2NHCH_2CH_2NHCH_2CH_2NH_2$
- $H_2C=CH-C(O)O-CH_2CH_2N$(piperazine)$NCH_2CH_2SO_2OH$

TABLE III-continued
Monomers

[Structures shown: N-methylpiperazine acrylamide; N-benzylpiperazine acrylamide; CH₂=C(CH₃)—C(O)—OCH₂CH₂N-piperazine-N—CH₂CH₂SO₂OH; acrylamide and methacrylamide derivatives with CH₂O/CH₂OH groups]

In the monomers of Formula V, $R_5$ is preferably H, halogen or alkyl, and one of $R_8$ and $R_9$ is H or alkyl.

The monomers of Formula V may be used alone, in combination with one another, or in combination with one or more comonomers of Formula I. The preferred comonomer of Formula I for such combination is N,N-dimethylacrylamide. Preferably, the comonomer of Formula I is present in an amount of up to about 80 volume % based on total volume of comonomers. However, it has been found hat a mixture of up to about 98 volume % N,N-dimethylacrylamide with a hydrophilic comonomer such as hydroxyethylacrylamide produces an aqueous gel with outstanding resolution for a variety or proteins.

The cross-linking agents utilized with the monomers of Formula V are divinyl compounds having either two amide functionalities, two ester functionalities or one amide and one ester functionality. Although thioanalogs may be utilized,, compounds wherein X=O are preferred. A can be a lipophilic unit such as an alkyl group, an alkenyl group, an alkynyl group, a cycloalkyl group, a heterocyclic group, an aromatic group, a steroidal ring, a fatty acid chain or a lipid chain. Alternatively, A may be a hydrophilic moiety such as an aliphatic or alicyclic polyol, a simple or amino sugar, an aromatic or heterocyclic ring with polar substituents such as —OH, —NH₂, —SH, —SO₂OH or —PO₄⁻³. Examples of suitable cross-linking agents include but are not limited to those set forth in Table IV. Thioanalogs of the agents set forth in Table IV would, of course, also be suitable.

TABLE IV
Cross-Linking Agents of Formula VI

Hydrophilic

| | |
|---|---|
| CH₂OC(O)CH=CH₂<br>\<br>(CHOH)ₙ<br>/<br>CH₂OC(O)CH=CH₂ | CH₂NHC(O)CH=CH₂<br>cyclohexane-O<br>NHC(O)CH=CH₂ |
| CH₂NHC(O)CH=CH₂<br>\<br>(CHOH)ₙ<br>/<br>CH₂NHC(O)CH=CH₂ | CH₂OC(O)CH=CH₂<br>cyclohexane-O<br>NHC(O)CH=CH₂ |
| CH₂NHC(O)CH=CH₂<br>\<br>(CHOH)ₙ<br>/<br>CH₂OC(O)CH=CH₂ | CH₂OC(O)CH=CH₂<br>cyclohexane-O<br>OC(O)CH=CH₂ |

Lipophilic

H₂C=HC—C(O)—NH(CH₂)₃NH(CH₂)₄NH(CH₂)₃NH—C(O)—CH=CH₂

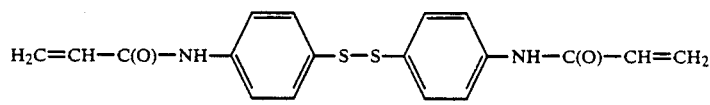
H₂C=CH—C(O)—NH—⌬—S—S—⌬—NH—C(O)—CH=CH₂

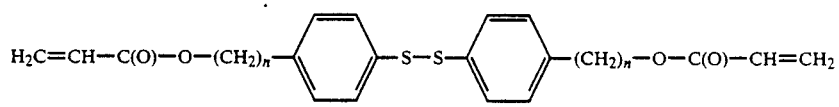
H₂C=CH—C(O)—O—(CH₂)ₙ—⌬—S—S—⌬—(CH₂)ₙ—O—C(O)—CH=CH₂

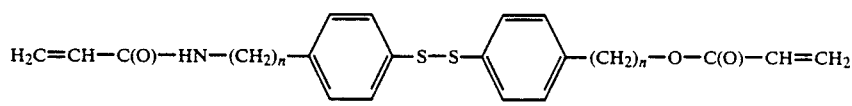
H₂C=CH—C(O)—HN—(CH₂)ₙ—⌬—S—S—⌬—(CH₂)ₙ—O—C(O)—CH=CH₂

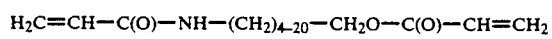
H₂C=CH—C(O)—NH—(CH₂)₄₋₂₀—CH₂O—C(O)—CH=CH₂

-continued
Lipophilic
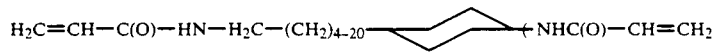
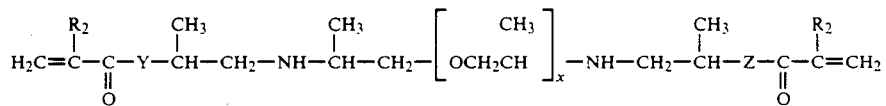
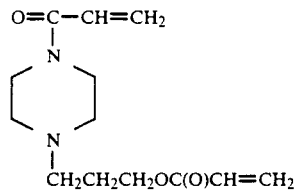
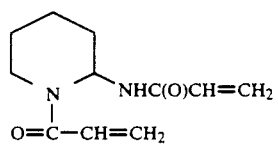
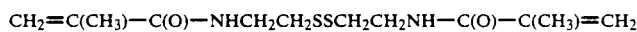
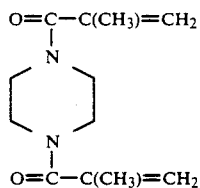
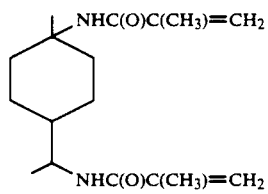
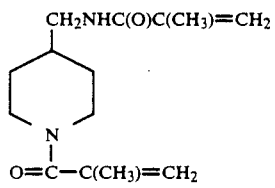
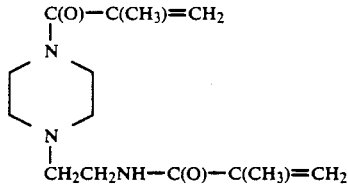
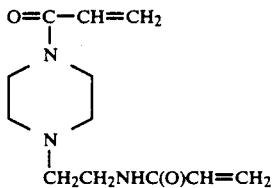

-continued

Lipophilic

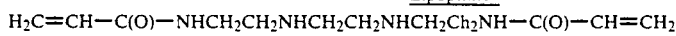
$H_2C=CH-C(O)-NHCH_2CH_2NHCH_2CH_2NHCH_2Ch_2NH-C(O)-CH=CH_2$

Specifically preferred cross-linking agents of Formula VI include ethyleneglycol dimethacrylate, and bisacrylate, bisacrylamide and acrylate/acrylamide derivatives of polymethylenehydroxyamines, e.g., compounds of Formula IV.

To prepare the polymer gels of this invention, the monomer(s) and cross-linking agent(s) are dissolved or dispersed in aqueous medium (water or a mixture of water with other organic solvents such as dimethylformamide) to prepare an aqueous solution or dispersion in which the crosslinking polymerization reaction is carried out. It is important that the polymerization reaction be carried out in the absence of oxygen. The relative amounts of monomer and cross-linking agent used will vary with the application for which the gel is to be used. Generally, however, the crosslinking agent can be employed in an amount of approximately 1 to 30 wt. %, preferably 2 to 10 wt. %, based on the total weight of the monomer and the crosslinking agent. The preferable gel concentration is such that the amount of monomer and cross-linking agent in the gel is 3% to 15% by weight.

The crosslinking polymerization reaction by which the novel gels of this invention are prepared is generally carried out in an aqueous medium and can be initiated by known initiators or polymerization catalysts. Suitable free radical-providing catalyst systems are benzoyl peroxide, t-butylhydroperoxide, lauroyl peroxide, cumene hydroperoxide, tetralin peroxide, acetyl peroxide, caproyl peroxide, t-butylperbenzoate, t-butyldiperphthalate, methylethylketone peroxide, hydrogen peroxide-Fe2+-ascorbic acid, riboflavin-light, and various persulfate salts in conjunction with N,N,N,'N'-tetramethylethylenediamine (TEMED), diethylmethylaminediamine (DEMED), B-dimethylaminopropionitrile or similar reagents and ammonium persulfate-metabisulfite. Another class of free radical generating catalysts are azocatalysts such as azodiiosobutyronitrile, azodiisobutryamide, azobis (dimethylvaleronitrile) azobis(methylbutyronitrile, dimethyl, diethyl, or dibutylazobismethylvalerate. These and similar reagents contain a N,N double bond attached to aliphatic carbon atoms, at least one of which is tertiary. The amount and type of catalyst and initiator is generally indicated by the nature and concentrations of the monomer and crosslinkers used. The optimum amount of catalyst is also affected by the presence of any accompanying impurities. Generally speaking, however, the catalyst can be employed in the amount of approximately 0.3 to 5 wt. % based on the total amount of the monomer and crosslinking agent. The preferred initiator and catalyst system is TEMED or DEMED and a persulfate salt.

Various buffer systems, denaturing agents or other modifiers (as required by the technique), may be included in the polymerization mixture. Examples of buffer systems suitable for use in the invention are:

| COMMON BUFFER SYSTEMS USED IN ELECTROPHORESIS | |
|---|---|
| Buffer | pH |
| Citrate-phosphate | 3.2 |
| Succinate | 5.2 |
| Phosphate-magnesium sulfate | 6.8 |
| Tris-EDTA-acetate | 7.2 |
| Tris-HCl-magnesium sulfate | 7.4 |
| Tris-EDTA-acetate | 7.8 |
| Tris-magnesium chloride | 8.0 |
| Tris-EDTA-borate | 8.3 |
| Tris-EDTA-borate | 8.6 |
| Tris-EDTA-lactate | 8.6 |
| Tris-veronal | 8.6 |
| Veronal | 9.2 |
| Tris-EDTA-borate | 9.5 |
| Tris-EDTA-phosphate | 8.6 |
| Tris-glycine | 8.8 |
| Tris-glycine-SDS | 8.8 |
| Sodium phosphate | 7.5 |
| Sodium-phosphate SDS | 7.5 |
| Ethanolamine/GABA* | 9.5–10 |
| Tris/acetate/GABA | 9.6–10.2 |
| Ammediol/GABA | 9.6–10.2 |
| Ammediol/HCl | 9.6–10.2 |
| Jeffamine series** | 9.6–10.2 |
| Tris-HCl | 9.3–9.6 |

*GABA = gamma, amino butyric acid
**Jeffamine series = polymethylenehydroxyamines of the type sold by Texaco Corporation Tests have indicated that the preferred buffer may vary both with the particular polymer matrix utilized and the desired application. For example, the gel prepared below in Example 1 and described below as "Gel I" is particularly useful for electrophoresis of DNA. The buffer system Tris/borate/EDTA has utilized with this gel with great success; excellent results have also been obtained using Tris/acetate/EDTA, Tris/phosphate/EDTA and Tris/glycylglycine buffer systems. The gel prepared below in Example 5 and described below as "Gel III" is particularly useful for electrophoresis of proteins. The buffer tris/glycine has been used with this gel with excellent results. Also, N-acrylamidepiperazine-3-propanyl acrylate (See Example 10) has been used in place of the N,N-methylenebisacrylamide crosslinking agent with excellent results. Finally, the gel prepared below in Example 9 and described below a "Gel IV" is particularly useful for sequencing of DNA. Best results have been achieved with this gel using the following buffer systems: ethanolamine/GABA, tris/acetate/GABA, and ammediol/GABA.

It is often preferred to incorporate in the gel a urea modifier to maintain the samples in a denatured state. The modifier can be used in an amount of approximately 40 to 60 wt. % based on the volume of the aqueous gel containing the monomer and crosslinking agent.

For best results in gel handleability, low background staining and good banding patterns, denaturing agents or detergents such as 0.1 to 1% of sodium dodecylsulfate (SDS) and 0.01 to 2% of polyoxyethylenes should also be incorporated in the gel. For example, when the cross-linking agent is the preferred ethyleneglycol dimethacrylate, it has been found that best results are achieved by using a polyoxyethylene of molecular weight of about 2000.

Other specific examples of denaturing agents which may be incorporated into the electrophoretic media of the invention include 1,3-dicyclohexylurea; 1,3-dibutyl 2-thiourea; 1,1-dimethylurea; 1,3-dimethylurea; 1,3-diallylurea; caprolactam; caproic acid, N,N-dimethylamide; phenol; butyl urea; cetyl alcohol; N,N-dimethylformamide; N,N-dimethylformamide dicyclohexyl acesal; cyanoguanidine; acetamide; oleyl alcohol; butyl urea; 1,1-carbonylimidazide; sulfamide; 3-aminotriazole; carbohydrazide; ethylurea; thiourea; urethan; N-methylurethan; N-propylcarbamate; methyl alcohol; ethyl alcohol; isopropyl alcohol; n-propyl alcohol; t-butyl alcohol; isobutyl alcohol; n-butyl alcohol; t-amyl alcohol; allyl alcohol; ethylene glycol; glycerol; formamide; N,N-dimethylformamide; .N,N-diethylformamide; acetamide; propionamide; butyramide; pyridine; dioxane; acetonitrile; 3-aminotriazole and glycine.

It is also often preferred to incorporat.e in the gel as an additive to improve strength either glycerol or a polymethylenehydroxyamine (e.g., of the type sold by Texaco Corporation as "Jeffamines"). These molecules have a molecular weight range of about 230 to 2000, and as little as 2% (per volume of the entire gel composition) can significantly affect the characteristics of the gel. Up to about 14 volume % of the glycerol is required to obtain similar advantages.

As previously indicated, gels within the scope of this invention may be used for various applications as diverse as separation of proteins, DNA and DNA sequencing. The end uses of the gels will depend heavily on the monomer and cross-linking agent composition as well as on the nature of the additives such as buffers, detergents and catalysts contained in the overall electrophoretic medium. A medium which is suited to one use may not, and probably will not be, suited for another use. Examples of specifically preferred gel compositions according to this invention are presented below. Gel I has been found to be particularly useful for electrophoresis of DNA strands, Gel III has been found to be particularly useful for the electrophoresis of proteins, and Gel IV has been found to be particularly useful for DNA sequencing.

| Gel I | |
|---|---|
| Major Components: | |
| N,N'-Dimethylacrylamide | 11 ml |
| Ethyleneglycol dimethacrylate | 1.2 ml |
| Urea and glycerol | optional |
| Polyoxyethylene (Tween 20) | 2 ml |
| pH Buffer: | |
| Tris | 1.08 g |
| Boric acid | 0.55 g |
| EDTA | 0.075 g |
| Water added: Final volume | 100 ml |
| Polymerization initiator: | |
| Ammonium persulfate (10 wt % aqueous solution) | 0.8 ml |
| TEMED | 30 µl |
| Gel II | |
| Major Components: | |
| N,N'-Dimethylacrylamide | 11 ml |
| Ethyleneglycol dimethacrylate | 1.2 ml |
| Other Ingredients: | |
| Polymethylenehydroxyamine (Jeffamine C-346*) or | 1.2 ml |
| (Jeffamine D-400*) | 0.4 ml |
| Polyoxyethylene (Tween-20) | 2 ml |
| Urea | optional |
| pH Buffer: | |
| Tris (hydroxymethyl)amino methane | 1.08 g |
| Boric acid | 0.55 g |
| EDTA | 0.075 g |
| Water added: Final volume | 100 ml |
| Polymerization Initiator: | |
| Ammonium persulfate (10 wt % aq soln) | 0.8 ml |
| TEMED | 0.03 µl |
| Gel III | |
| Major Components: | |
| N,N-Dimethylacrylamide | 10 ml |
| Hydroxyethylmethacrylate | 0.28 ml |
| N,N-Methylenebisacrylamide (1.4 wt/v aq. soln) | 20 ml |
| Other Ingredient: | |
| Sodium dodecylsulfate, 10% | 1 ml |
| pH Buffer: | |
| Tris HCl | 50 ml |
| Water added: Final volume | 100 ml |
| Polymerization Initiator: | |
| Ammonium persulfate (10 wt % aq soln) | 0.8 ml |
| TEMED | 0.12 ml |
| Gel IV | |
| Major Components: | |
| N,N-Dimethylacrylamide | 18 ml |
| N,N-Methylenebisacrylamide | 0.3 g |
| Other Ingredients: | |
| Polyethyleneglycol dimethacrylate | 0.15 ml |
| Dimethylformamide | 0.99 ml |
| Glycerol | 0.1 ml |
| Final volume with $H_2O$ | 100 ml |
| Running Buffer (20 ×): | |
| Gamma, amino-butyric acid | 12.6 g |
| Ethanolamine | 37.1 ml |
| Jeffamine M-600 | 0.01 ml |
| Water added: Final volume | 100 ml |
| Final pH | 11 |
| Details of Polymerization: | |
| Gel solution prepared above | 75 ml |
| Ammediol-HCl (0.5M, pH 9.6) | 25 µl |
| TEMED | 220 µl |
| Ammoniumpersulfate (10%) | 500 µl |
| Electrophoresis carried out with 1 × running buffer | |

*(Jeffamine is sold by Texaco Chemical Company; C-346 has a molecular weight of approximately 346, C-400 has a molecular weight of approximately 400)

Membranes made from the aqueous gel media of this invention generally have a thickness in the range of approximately 0.1 mm to approximately 3 mm, preferably in the range of approximately 0.2 to 1.5 mm. The gel membranes of this invention can also, however, be made very thin, e.g., to a thickness of less than 0.1 mm, and yet exhibit excellent resiliency and resolution.

The materials described herein for use as gels can also be prepared as porous, non-porous, or macroreticular beads of any dimension for use in electrophoretic applications. In preparing beads several polymerization conditions well known in the art can be used. A preferred method is suspension polymerization in a liquid which is not a solvent for the materials used. This method produces the polymer in the form of spheroid beads the size of which can be regulated and controlled by the composition of the suspending medium and the rate of agitation during polymerization. The determination of the most effective conditions vary from case to case, depending on the materials chosen, their amounts and relative proportions. Polymerization may also be carried out in the presence of a precipitant, i.e., a liquid which acts as a solvent for the mixture and is chemically inert under the polymerization conditions. The solvent must be present in such amounts as to exert little solvating action. On polymerization phase separation of the product takes place. The exact solvents used are determined and optimized empirically for each mixture. A typically used inverse suspension polymerization involves a small amount of water in a hexane solution stirred very fast with initiators present. The polymerizing materials will stay in the water droplets depending on their hydrophilic properties.

Beads prepared from the above described materials may also be useful for the separation of DNA, RNA, proteins and peptides in a chromatography format. Separation can be adjusted to occur via interaction or be based on size. Interactive chromatography can result from ion-exchange, hydrophobic, or other modes directly with the bead materials or with modifiers or substituted chemical groups added pre- or post-polymerization.

The materials described can also be used for the preparation of gels or beads, alone or in conjunction with other materials or attached to any surface, for the purpose of providing nutrients and support for bacterial or cellular growth for any purpose. Examples are polymerizing in and/or placing gels or beads alone or in conjunction with other materials in petri dishes or by coating (covalently or non-covalently) glass, metal, plastic, teflon, paper of any composition, polyvinylchloride, silica or other surfaces. Applications may include bacterial smears for diagnostic purposes or provisions of attachment sites for cell growth. A further example of such a material is polyvinylchloride papers impregnated with silica or glass. Coating of these surfaces with a function capable of participating in the polymerization process would allow direct polymerization and covalent attachment of the material to the support.

In addition to these applications it is also feasible to include into the polymerization mixture proteins, peptides, pharmaceuticals, silica, polymer particles of various sizes, or electron conductive materials. The above materials could be used for a variety of applications including drug delivery, artificial organs or parts thereof and plastic type conductors of electricity.

This invention will be further described by the following examples.

EXAMPLE 1

Preparation of Gel for Electrophoresis of Non-Denatured DNA

A solution containing N,N-dimethylacrylamide (11 ml), ethylene glycol dimethacrylate (1.2 ml), polyoxyethylene (Tween-20; 2 ml) and 10 ml of a Tris-borate-ethylenediaminetetraacet acid (TBE) buffer concentrate (TBE, 108 g Tris, 55 g boric acid, 40 ml 0.5 M ehtylenediaminetetraacetic acid (EDTA) in 1000 ml water, pH 8) was diluted with water to a final volume of 100 ml. The turbid solution was sonicated in vacuo for at least 1 minute. N,N,N$^1$,N$^1$-tetramethylethylenediamide (TEMED; 30 ul) and ammonium persulfate (0.8 ml; 10%) were added to the above degassed solution and thoroughly mixed. About 35 ml of the solution was poured between two glass plates (Hoeffer, 16×18 cm) with 1.5 mm teflon spacers prepared according to the art. A teflon sample well comb was inserted at the top of the glass plates. Polymerization was at room temperature (45 minutes). Polymerized gels were transparent.

Chemical Characterization

A typical DNA gel prepared according to the general procedure described above was repeatedly washed with water, methanol, DMF, chloroform, and methanol; dried in an oven at 60$^C$ for several weeks to give a white waxy solid analyzing: C, 58.02; H, 9.3; N, 12.53%. The solid gel was insoluble in DMSO.

Spectroscopic Characterization

The gels prepared as described above did not possess any fluorescence; excitation at 280 nm showed essentially no emission from these gels. The gels were transparent down to below 250 nm. FT-IR spectrum (KBr): The spectrum showed bands (cm$^{-1}$) at 3436 (water), 3100–2800 (C-H stretch), 1733 (ester carbonyl), 1635 (amid carbonyl) and no >C=CH$_2$ bands showing the absence of any monomer.

A hypothetical structure of the gel prepared according to Example 1 can be suggested as follows:

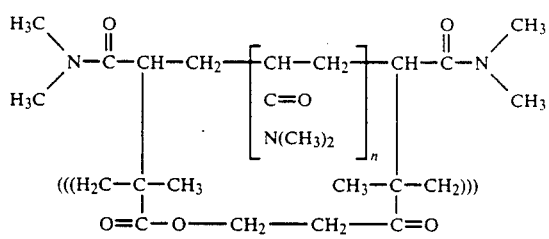

When this is compared to a hypothetical structure of the conventional acrylamide/N,N'-methylenebisacrylamide gels of the prior art, as shown below, the significantly different structure of the gels of this invention can be appreciated.

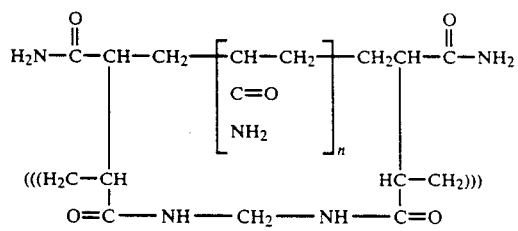

EXAMPLE 2

Electrophoresis of Non-Denatured DNA

Various nucleic acid molecular weight standards were obtained from commercial sources and prepared for electrophoresis by dilution (1:1) with TBE buffer, pH 8.0, containing 50% glycerol, 0.25% bromophenol blue or xylene cyanol green and 100 mm EDTA. Standards used were:

1. 1 kb ladder. This ladder contains double-stranded DNA fragments from 400 base pairs (bp) to 12000 bp in length formed by 12 repeats of a 1018 bp fragment derived from the yeast 2 u circle and the fragments 1636, 517, 506, 396, 344, 298, 220, 201, 154, 134 and 75 bp. 2. 123 bp ladder. This ladder contains double-stranded DNA from 100 to 4182 bp long formed by 34 repeats of 123 bp.

3. λ-Hind III. This ladder is composed of eight double-stranded fragments from 125 to 23100 bp.

4. φX-Hae III. This ladder contains 11 double-stranded fragments from 72–1353 bp.

2–10 μg total of each standard mixture were applied to the gel lanes and electrophoresis performed in a Hoeffer electrophoresis chamber (SE 600) at 5 mA. TBE buffer was used in the electrode chambers. Progress of the electrophoresis was monitored by movement of the dye which resolved into two bands; electrophoresis was stopped when the faster moving component reached halfway through the gel. The gel was removed from the glass plates and stained 20 minutes with ethidium bromide (20 μl, 100 mg/ml water) in 200 ml of TBE buffer. After rinsing with distilled water bands were visualized with UV light and separations photographed. Resolution of φX-Hae III, λ-Hind III, 123 bp and 1 Kb ladder is shown in FIG. 1.

A quantitative comparison of resolution of the gel of Example 1 ("DNA Gel") to agarose gel were made as follows:

Using the standard mixtures described above Resolution Challenge was defined as the number of components in a given sample relative to the degree of similarity between them i.e., base pair number. The smaller the differences in base pair number the greater the Resolution Challenge. Of the standards used, the 123 bp ladder is the most difficult to resolve. Resolution Efficiency was defined as the ability to resolve the available components in a single separation. Values for agarose were determined from optimal published data and internal laboratory results. Values for "DNA gel" were determined experimentally. Results are summarized in Table VI.

TABLE VI

| DNA Mixture | Resolution Challenge[1] | Efficiency Agarose[2] | DNA-Gel |
|---|---|---|---|
| 1 Kb | 0.04 | 74 | 91 |
| bp | 0.27[3] | 56 | 100 |
| φX-Hae III | 0.09 | 82 | 91 |
| λ-Hind III | 0.003 | 75 | 100 |

[1]Calculated by number of components to be resolved divided by average bp difference between components
[2]Calculated from published agarose separations and internal control gels.
[3]A large number represents a more difficult separation.

As shown in each case, a dramatic improvement in resolution was observed using the "DNA Gel", averaging 24% overall but 44% for the most difficult 123 bp standard. The DNA gel of Example 1 also demonstrated substantial resiliency and resistance to breakage and could be lifted and handled easily.

Figure 2:
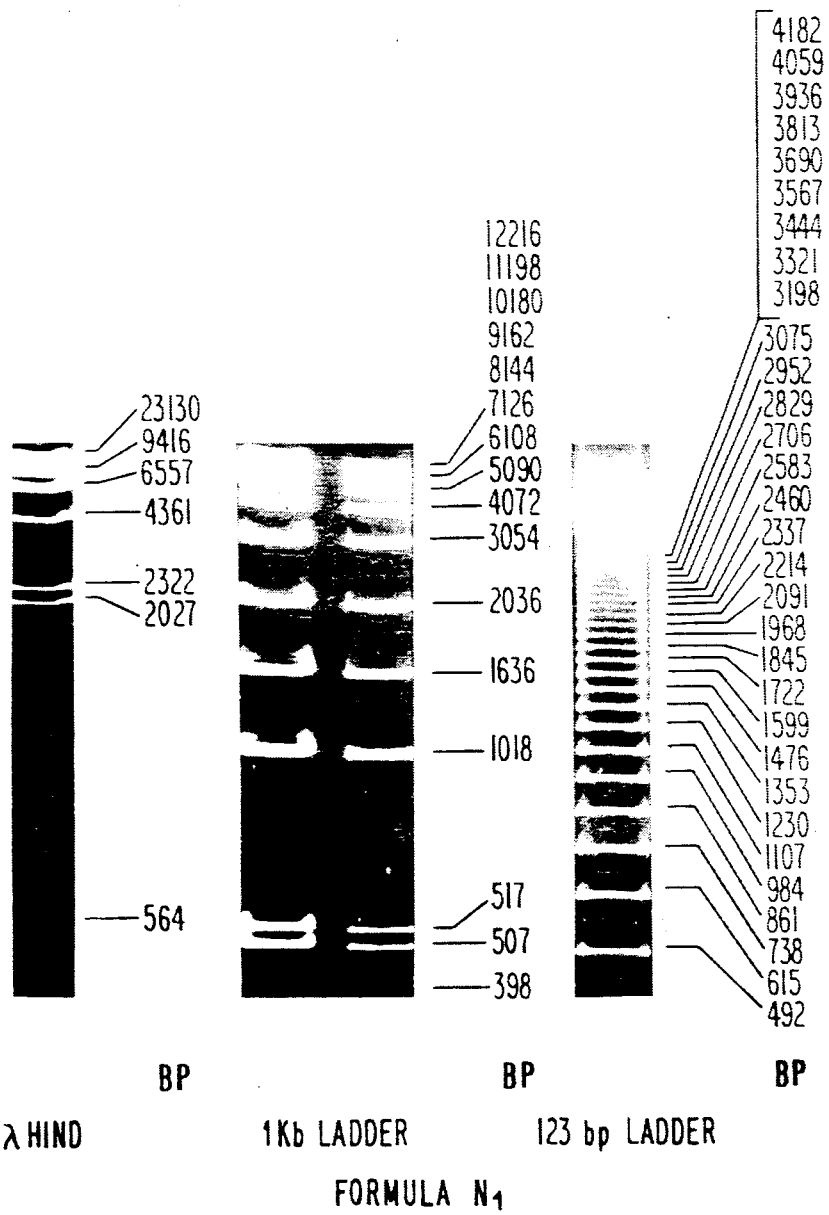
FIG. 2 shows the post-electrophoresis gel of FIG. 1 in aqueous solution.

The gel of Example 1, if left in aqueous solution, imbibes sufficient water to swell without band diffusion thereby enhancing resolution (see FIG. 2) and facilitating DNA recovery (see Example 3).

EXAMPLE 3

Recovery of DNA from DNA Gels

Recovery of DNA from gels prepared as described in Example 1 was examined by two methods: first, a simple salt elution of cut-out bands with gel homogenization, and, second, electroelution. Salt elution was examined using a 1Kb DNA (BRL standard) labelled with [γ-$^{32}$P]ATP using T4 polynucleotide kinase obtained from commercial sources according to the manufacturers, instructions. After electrophoresis, various localized fragments were excised from the gel. Cut-out bands were crushed or minced into finer pieces and 1 ml 1.5 M NaCl was added. Gel slices were incubated overnight (15 hr) at 37° C. with shaking. Following the incubation, supernatant and gel bits were separated by filtration or centrifugation, washed once with 1 ml H$_2$O, and DNA was precipitated with ethanol. The percentage recovery was determined by liquid scintillation counting of $^{32}$P-labelled DNA recovered and remaining in the gel bits. Results are presented in Table VII. Electroelution recovery of DNA from gel was also conducted, resulting in almost quantitative recovery.

TABLE VII

Recovery of DNA from DNA Gel of Example 1 and from Polyacrylamide Gel by the Salt Elution Method

| Fragment Size | % Recovery[a] Gel of Example 1 | Polyacrylamide |
|---|---|---|
| Less than 250 bp | 97.1 | 98.3 |
| 250–1000 bp | 81.1 | 69.2 |
| 1000–3000 bp | 57.7 | 35.5 |

[a]% Recovery was % of total DNA recovered by elution in 1.5M NaCl as determined by scintillation counting of remaining gel bits vs. supernatant in at least three experiments.

EXAMPLE 4

DNA Transfection

While DNA can be recovered from agarose gels in high yield, contaminants which hinder DNA ligation and transfection or transformation persist even with the highest grades of agarose. DNA can be recovered from conventional polyacrylamide gels (with somewhat more difficulty) without these contaminants but the resolution range and capacity are far less than agarose. DNA extracted from the gel of Example 1 and agarose gel were tested for transfection efficiency (i.e., the ability to transfer a gene as a function of the amount of DNA recovered). The experimental details are as follows:

Plasmid pBR 322 was obtained from commercial sources. This plasmid contains the gene for ampicillin resistance. The plasmid was digested with EcoR$_1$ and BamH$_1$ (in duplicate) and one duplicate digest was subjected to agarose electrophoresis and the other subjected to DNA gel o Example 1 electrophoresis. Enzyme digests and agarose electrophoresis were performed according to the art. After electrophoresis the digested DNA fragments were localized with ethidium bromide staining and cut out from the gels. The agarose prepared material was electroeluted according to the art. The DNA gel electrophoresed bands were extracted with chloroform-phenol-buffer (1:1:1) at 37° C. for 20 minutes without homogenizing the gel. Fragments were recovered (approximately 1.5% of the total DNA) from the aqueous layer of the chloroform-phenol-buffer extract by ethanol precipitation. Approximately 85% of the total DNA was recovered from the agarose gel by electroelution and ethanol precipitation. The recovered DNA from each gel was religated using T$_4$ DNA ligase overnight at 14° C. Ligated DNA wa transfected into HB 101-cells and plated in duplicate on Luria Broth plates containing ampicillin (100 ug/ml). The number of colonies produced, indicating successful ligation and transferral of the gene, is shown in Table VIII. Controls were uncut plasmid, plasmid fragments without religation and no plasmid.

TABLE VIII

| HB 101 Cell (Dilution) | Number of Colonies (Agarose) | (DNA Gel) |
|---|---|---|
| 1:100 | 0 | 1 |
| 1:25 | 67 | 41 |
| 1:1 | 164 | 170 |

These results demonstrate a similar number of colonies produced for 1.5% of the total DNA (DNA gel)

versus 85% of the total DNA recovered from agarose. The suggestion is a 56-fold increase in transfection efficiency using DNA gel.

EXAMPLE 5

Preparation of Base Gel for Electrophoresis of Proteins

A solution containing N,N-dimethylacrylamide (10 ml), hydroxyethyl methacrylate (0.28 ml), Tris HCl buffer (50 ml; 0.75 M; pH 8.8), sodium dodecylsulfate (SDS, 1 ml; 10%) and N,N-methylenebiscarylamide (20 ml; 1.4%) was diluted with distilled water to a final volume of 100 ml. The solution was thoroughly mixed; the resulting clear solution was degassed by sonication in vacuo. N,N,N$^1$,N$^1$-tetramethylethylenediamine (TEMED, 0.12 ml) and ammonium persulfate (0.8 ml; 10%) were added to the above solution and the solution was thoroughly mixed. The resulting clear solution (approximately 30 ml) was poured between two glass plates (16×18 cm with 1.5 mm thick teflon spacers) fitted to a Hoeffer electrophoresis apparatus. n-Butanol (approximately 5 ml) was layered over the top of the solution within the plates to prevent any aeration of the gel. The solution within the plates polymerized at room temperature in about 30 minutes, determined by running a control experiment in a test tube. n-Butanol was removed by decantation; and the top of the gel washed thoroughly with distilled water.

Spectroscopic Characterization

The gels did not possess any fluorescence; excitation at 280 nm shows essentially no emission from these gels. The gels were transparent down to below 250 nm. FT-IR spectrum (KBr): The spectrum showed bands (cm$^{-1}$) at 3436 (water), 3100–2800 (C-H stretch), 1733 (ester carbonyl), 1635 (amide carbonyl) and no >C=CH$_2$ bands showing the absence of any monomer.

EXAMPLE 6

Preparation of Stacking Gel for Electrophoresis of Proteins

A solution containing N,N-dimethylacrylamide (4 ml), Tris HCl buffer (34 ml; 0.375 M; pH 6.6), sodium dodecylsulfate (SDS, 1 ml; 10%), and N,N-methylenebisacrylamide (10 ml; 1.4%) was diluted with distilled water to a final volume of 100 ml. The solution was sonicated in vacuo for about 1 minute. N,N,N$^1$,N$^1$-tetramethylethylendiamine (TEMED, 0.1 ml) and ammonium persulfate (0.1 ml; 10%) were added to the degassed solution and thoroughly mixed. The resulting clear solution (approximately 10 ml) was poured over the top of the base gel which was scrupulously dried with filter paper. Sample wells were crated using Teflon well combs inserted into the gelling solution prior to polymerization (20 minutes at room temperature).

EXAMPLE 7

Electrophoresis of Proteins Using Base Gel alone or with Stacking Gel

Figure 3:
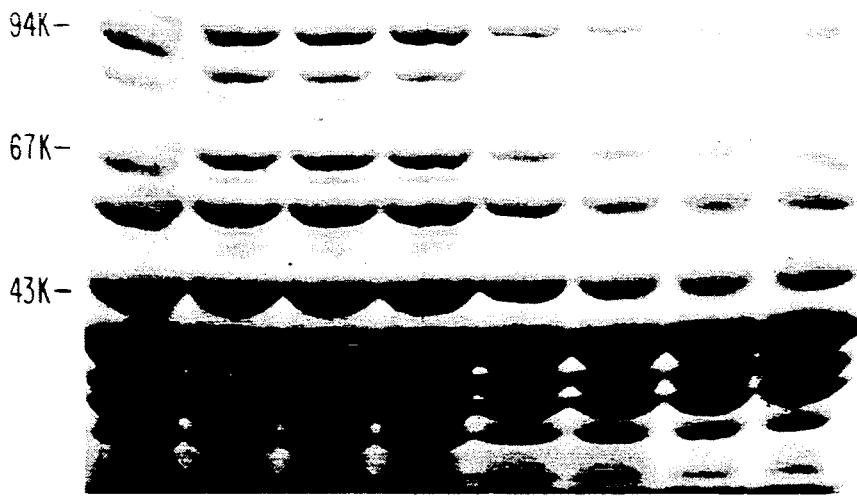
FIG. 3 shows an electrophoretic separation of guinea pig muscle extract (100 ug/lane) using the base gel of Example 5.
Figure 4:
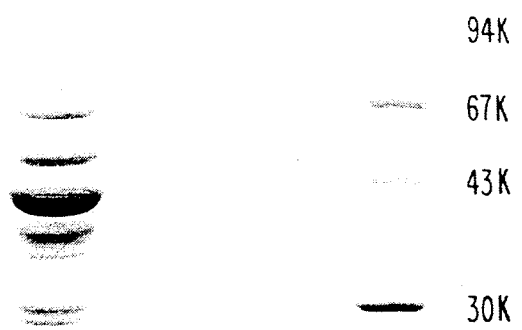
FIG. 4 shows an electrophoretic separation of guinea pig muscle extract using the stacking gel of Example 6 and N,N-diemthylacrylamide gradient (7–12%).

Protein samples were loaded in each well with sample buffer containing SDS (10μl, 10%), sucrose (10 μl; 100%), bromophenol blue (1 μl), _-mercaptoethanol (1 μl) and Tris HCl (10 ul; 0.375 M, pH 6.6) in a final volume of 100 μl. Electrophoresis was carried out overnight at 5 mAmp or for 3 hours at 30–50 mAmp with cooling in an electrophoresis chamber containing 4 liters of buffer solution diluted from a 10x stock (Tris 12 g, glycine 57.6 g, and SDS 1 g in 100 ml water). Gels were stained with Coomasie Brilliant Blue R-250 and destained with 20% methanol, 5% citric acid. FIG. 3 shows electrophoresis of guinea-pig muscle extract using base gel. FIG. 4 shows electrophoresis of guinea-pig muscle extract using stacking gels and N,N-dimethylacrylamide gradient (7–12%). Gels prepared under different sets of conditions such as 7–15% of N,N-dimethylacrylamide, 0.07–0.5% of bisacrylamide, 0.14–2.4% of hydroxyethylmethacrylamide differed significantly in their mechanical strength, band shape, and resolving power.

EXAMPLE 8

Gel for Isoelectric Focusing

N,N-Dimethylacrylamide (4 ml) was added to an aqueous solution (final volume: 5 ml) containing ethyleneglycol dimethacrylate (0.3 ml), TEMED (15 μl), Tween-20 (1 ml), buffalytes (12.5 ml; pH 3–10), and urea (12 g). (Alternatively, ampholytes were added in place of buffalytes to 1% final concentration.)

Figure 5:
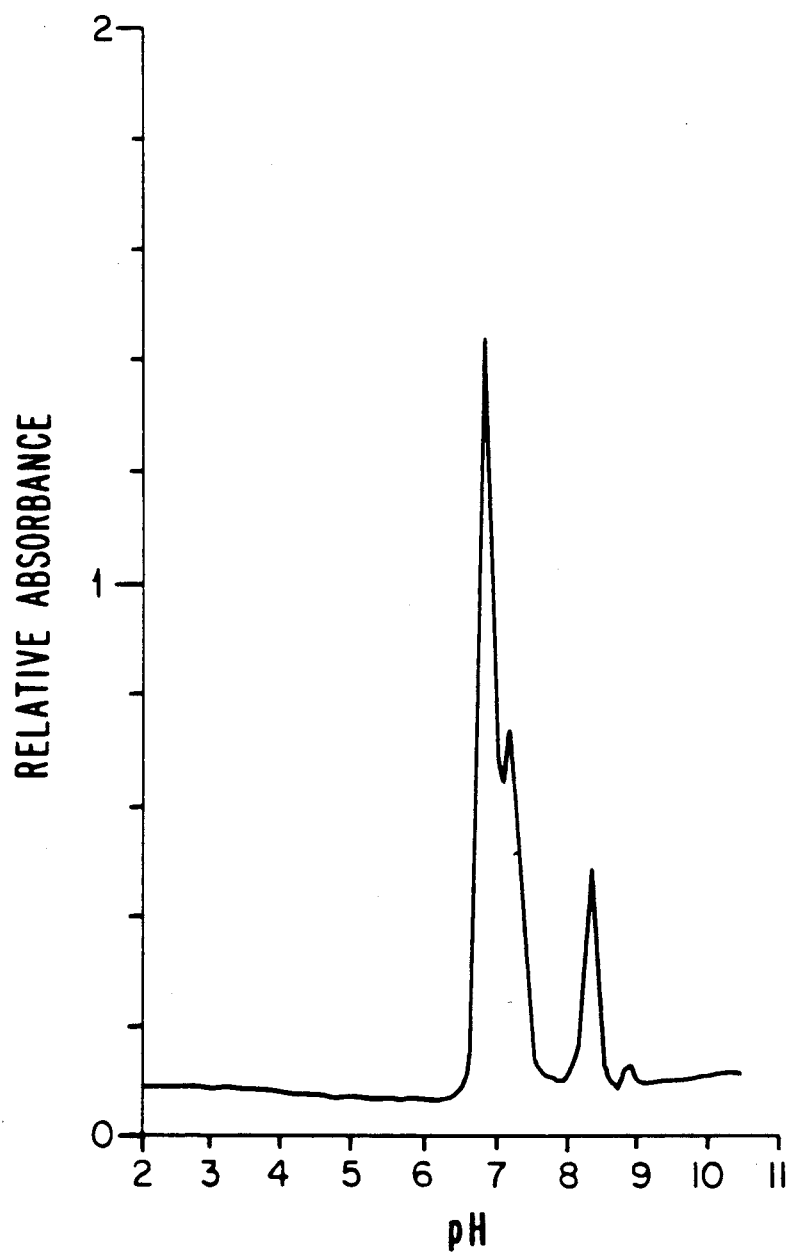
FIG. 5 shows densitometer tracing of isoelectric focusing of hemoglobin.

The solution was stirred and degassed with sonication for 2 minutes; ammonium persulfate (10%; 0.3 ml) added to the resulting solution. The gelling solution was poured between two glass plates (16×18 cm) separated by 1.5 mm teflon spacers. A preparative sample comb was used. The solution was polymerized for 45 min to give a clear gel; 5 ml of a 10 mg/ml solution of hemoglobin containing 10% glycerol was loaded. This was overlaid with 5% glycerol; the upper buffer was 0.2 M NaOH and the lower buffer was 0.2 M H$_2$SO$_4$. Focusing was performed at 20 mA until the hemoglobin had myrated to its isoelectric point (approximately 2 hr). FIG. 5 shows densitometer tracing of isoelectric focusing of hemoglobin.

EXAMPLE 9

A gelling solution was prepared by the addition of 0.4 g bis-acrylamide to 8 ml of dimethylacrylamide and 0.3 ml polymethylenehydroxyamine (Jeffamine C-346) and 91.7 ml of water. The solution was stirred until the bis-acrylamide dissolved (10 min) and 50 ul of TEMED were added. The gelling solution was then degassed with sonication and 2 ml of a 10% solution of ammonium persulfate were added. The mixture was poured between two glass plates separated by 0.4 mm spacers to the top and a sample well comb inserted. The length of the gel was 36 cm.

A pre-electrophoresis at 1000V was performed for 45 min. after which sequencing samples of DNA were applied. The samples used were the M13 primer and Sequenase reactions performed using $^{32}$P labelled nucleosides according to the art. The gel had excellent properties when used for the resolution of proteins.

EXAMPLE 10

The compound N-acrylamide-piperazine-3-propanyl acrylate, having the formula

Figure 6:
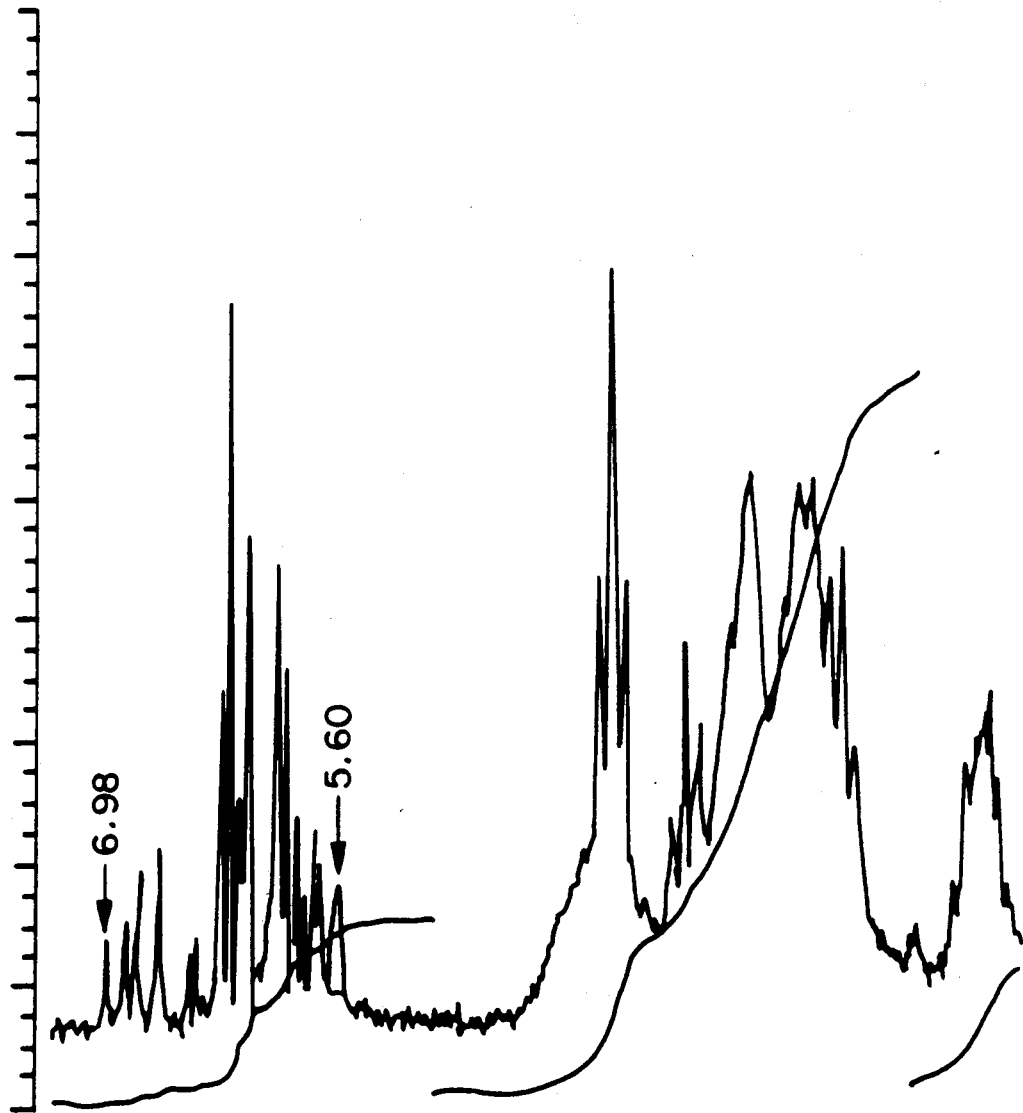
FIG. 6 is an NMR spectrum for the compound N-acrylamide-piperazine-3-propanyl acrylate, prepared in Example 10.
Figure 7:
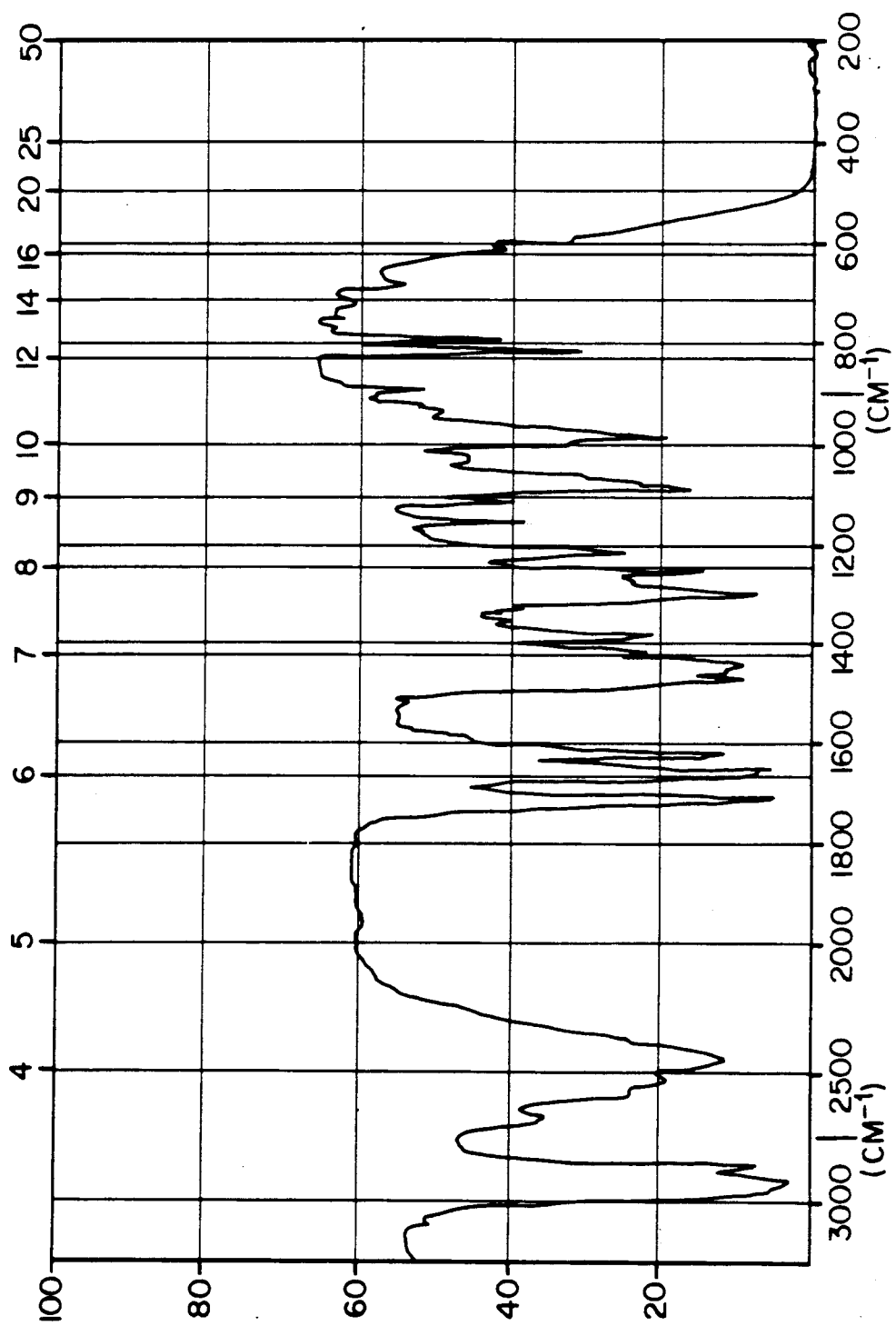
FIG. 7 is an IR spectrum for the compound N-acrylamide-piperazine-3-propanyl acrylate, prepared in Example 10.

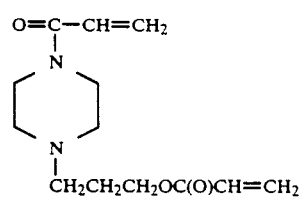

was prepared by adding dropwise two molar equivalents of acryloylchloride to a solution of piperazine 3-propanol dissolved in chloroform and containing an excess of base. The reaction was carried out overnight. Careful workup gave a product which was crystallized from methanol. Elemental analysis showed: Found: C, 50.88; H, 7.26; N, 9.21% $C_{13}H_{20}N_2O_3.3H_2O$ (306) Calculated: C, 50.98; H, 8.49; N, 9.15% NMR and IR spectra for the compound are provided in FIGS. 6 and 7, respectively.

Gels were made using the N-acrylamide-piperazine-3-propanyl acrylate as a cross-linker for N,N-dimethylacrylate as monomer and were found to have excellent properties for resolving proteins under electrophoretic conditions.

EXAMPLE 11

Additional gels were made using the general method set forth in Example 1 and using (1.2%) ethyleneglycol dimethacrylate cross-linking agent. The gels and certain of their characteristics are set forth below in Table IX in which monomers and comonomers are described in volume % based on total volume of the gel formulation.

TABLE IX

| | A. Gel | |
|---|---|---|
| Gel | Monomer Conc. (%) | Comonomer Conc. (%) |
| A | $CH_2=CH-C(=O)-N(CH_3)_2$ (12%) | $CH_2=C(CH_3)-C(=O)-N-CH_2CH=CH_2$ (1%) |
| B | $CH_2=CH-C(=O)-N(CH_3)_2$ (10%) | $CH_2=CH-C(=O)-NHC_2H_5$ (2%) |
| C | $CH_2=CH-C(=O)-N(CH_3)_2$ (10%) | $CH_2=CH-C(=O)-NH-nC_4H_9$ (2%) |
| D | $CH_2=CH-C(=O)-N(CH_3)_2$ (10%) | $CH_2=CH-C(=O)-NH-CH_3$ (2%) |
| E | $CH_2=CH-C(=O)-N(CH_3)_2$ (6%) | $CH_2=CH-C(=O)-N(C_2H_5)_2$ (6%) |
| F | $CH_2=CH-C(=O)-N(CH_3)_2$ (6%) | bornyl acrylate $OCCH=CH_2$ (5%) |
| G | $CH_2=CH-C(=O)-N(CH_3)_2$ (6%) | furfuryl acrylate (furan-CH_2OCCH=CH_2) (6%) |
| H | $CH_2=CH-C(=O)-NH-CH_3$ (12%) | $CH_2OCCH=CH_2$ / $CHOH$ / $CH_2OH$ (1.2%) |
| I | $CH_2=CH-C(=O)-N(CH_3)_2$ (10%) | $CH_2=CH-C(=O)-N(C_2H_5)_2$ (2%) |
| J | $CH_2=CH-C(=O)-N(CH_3)_2$ (10%) | $CH_2=CH-C-NH-CH_3$ (2%) |
| K | $CH_2=CH-C(=O)-N(CH_3)_2$ (10%) | $CH_2=C(CH_3)-C(=O)-O-CH_2CH_2OH$ (2%) |

| | B. Gel Characteristics | | |
|---|---|---|---|
| Gel | Resolution of DNA Fragments | Mechanical Strength | Swelling Characteristics |
| A | Good | Good | No swelling |
| B | Good | Good | Some swelling |
| C | Good | Good | No swelling |
| D | Good | Good | No swelling |
| E | Good | Good | Some swelling |
| F | Good | Good | No swelling |
| G | — | Poor | Poor |
| H | — | Poor | Poor |
| I | Good | Good | Some swelling |
| J | Good | Good | No swelling |
| K | — | Good | Some swelling |

(A rating of "good" was given for better performance and mechanical strength and swelling characteristics when compared to polyacrylamide gels run under identical conditions.)

What is claimed is:

1. An electrophoretic medium comprising an aqueous gel consisting essentially of the product formed by crosslinking polymerization in the presence of aqueous medium and in the absence of oxygen of
    one or more monomers selected from compounds of the formula

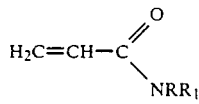 (I)

where
R = alkyl, optionally mono-substituted with —OH or with —C(O)CH$_2$C(O)CH$_3$;
R$_1$ = H or alkyl, optionally mono-substituted with—OH or with —C(O)CH$_2$C(O)CH$_3$; and
one or more cross-linking agents selected from compounds of the formula

where
m = an integer of 1 or more;
R$_2$ = methyl; and
X is selected from O and S.

2. An electrophoretic medium of claim 1 where R$_1$ is other than H.

3. An electrophoretic medium of claim 1 where R = R$_1$.

4. An electrophoretic medium of claim 3 where R and R$_1$ are methyl.

5. An electrophoretic medium of claim 1 where R$_2$ = H.

6. An electrophoretic medium of claim 1 where the crosslinking agent is ethyleneglycol dimethacrylate.

7. An electrophoretic medium of claim 1 where the monomer is N,N-dimethylacrylamide and the cross-linking agent is ethyleneglycol dimethacrylate.

8. An electrophoretic medium of claim 7 which further comprises a polyethylenehydroxyamine.

9. An electrophoretic medium of claim 7 which further comprises about 0.01 to 2% of a polyoxyethylene having a molecular weight of about 2000.

10. An electrophoretic medium of claim 7 which further comprises a buffer selected from the group consisting of tris/borate/EDTA, tris/acetate/EDTA, tris/phosphate/EDTA and tris/glycylglycine.

11. An electrophoretic medium of claim 7 which further comprises a polyethylenehydroxyamine, about 0.01 to 2% of a polyoxyethylene having a molecular weight of about 2000, and a buffer selected from the group consisting of tris/borate/EDTA, tris/acetate/EDTA, tris/phosphate/EDTA and tris/glycylglycine.

12. An electrophoretic medium of claim 1 which further comprises one or more additives selected from urea, glycerol and polymethylenehydroxyamines.

13. An electrophoretic medium of claim 1 which further comprises a denaturing agent.

14. An electrophoretic medium of claim 13 where said denaturing agent is selected from sodium dodecyl sulfate and polyoxyethylenes.

15. An electrophoretic medium comprising beads formed by crosslinking polymerization of
one or more monomers selected from compounds of the formula

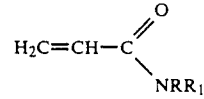

where
R = alkyl, optionally mono-substituted with —OH or with —C(O)CH$_2$C(O)CH$_3$;
R$_1$ = H or alkyl, optionally mono-substituted with—OH or with —C(O)CH$_2$C(O)CH$_3$; and
one or more cross-linking agents selected from compounds of the formula

where
m = an integer of 1 or more;
R$_2$ = methyl; and
X is selected from O and S.

* * * * *

UNITED STATES PATENT AND TRADEMARK OFFICE
CERTIFICATE OF CORRECTION

PATENT NO. : 5,055,517

DATED : October 8, 1991

INVENTOR(S) : Robert SHORR et al.

It is certified that error appears in the above-identified patent and that said Letters Patent is hereby corrected as shown below:

Column 1, line 67, delete "correction" and insert therefor --convection--.

Column 2, line 7-8, delete "approximately0.3" and insert therefor --approximately 0.3--.

Column 4, line 3 delete "-C(O)CH$_2$C(O)CH$_3$:" and insert therefor -- -C(O)CH$_2$C(O)CH$_3$;--

Column 5, line 51, delete "N,N-diemthylacrylamide" and insert therefor --N,N-dimethylacrylamide--. (US)

Column 6, line 57, delete "ma" and insert therefor --may--.

Column 11, line 33, delete "hat" and insert therefor --that--.

Column 16, line 50, delete "a" and insert therefor --as--.

Column 19, line 51, delete "ethylenediaminetetraacet" and insert therefor --ethylenediaminetetraacetic--.

Column 21, line 58-59, delete "manufacturers," and insert therefor --manufacturers'--.

Column 22, line 37, delete "o" and insert therefor --of--.

UNITED STATES PATENT AND TRADEMARK OFFICE
CERTIFICATE OF CORRECTION

PATENT NO. : 5,055,517

DATED : October 8, 1991

INVENTOR(S) : Robert SHORR et al.

It is certified that error appears in the above-identified patent and that said Letters Patent is hereby corrected as shown below:

Column 7 and 8, Lines 28 through 33 (within "Table 1") delete
"

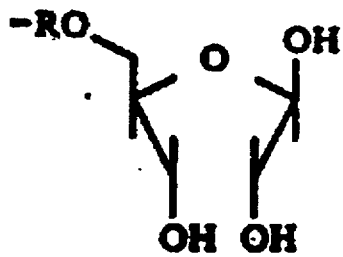

"
and insert therefor --

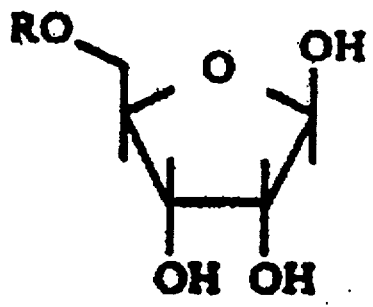

--

UNITED STATES PATENT AND TRADEMARK OFFICE
CERTIFICATE OF CORRECTION

PATENT NO. : 5,055,517

DATED : October 8, 1991

INVENTOR(S) : Robert SHORR et al.

It is certified that error appears in the above-identified patent and that said Letters Patent is hereby corrected as shown below:

Column 7 and 8, Lines 35 through 42 (within "Table 1") delete
"
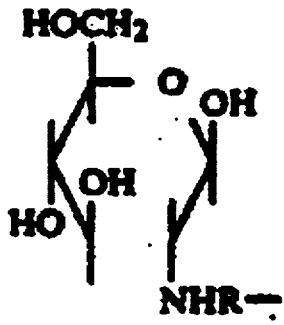
"
and insert therefor --
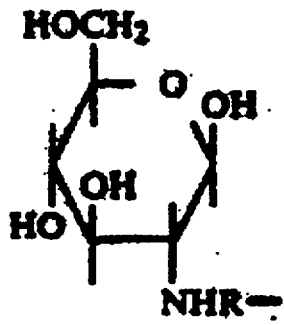
--

UNITED STATES PATENT AND TRADEMARK OFFICE
CERTIFICATE OF CORRECTION

PATENT NO.  : 5,055,517
DATED       : October 8, 1991
INVENTOR(S) : Robert SHORR et al.

It is certified that error appears in the above-identified patent and that said Letters Patent is hereby corrected as shown below:

Column 7 and 8, Lines 52 through 57 (within "Table 1") delete

"

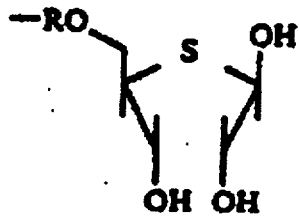

"

and insert therefor --

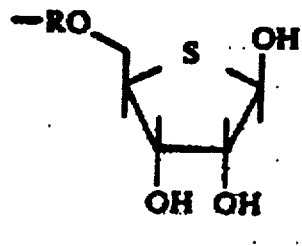

--

UNITED STATES PATENT AND TRADEMARK OFFICE
CERTIFICATE OF CORRECTION

PATENT NO. : 5,055,517

DATED : October 8, 1991

INVENTOR(S) : Robert SHORR et al.

Page 5 of 6

It is certified that error appears in the above-identified patent and that said Letters Patent is hereby corrected as shown below:

Column 7 and 8, Lines 59 through 64 (within "Table 1") delete

"
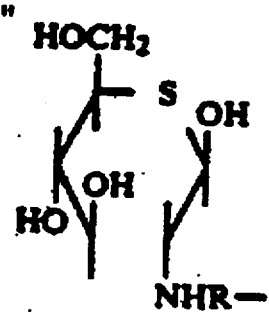
"

and insert therefor --

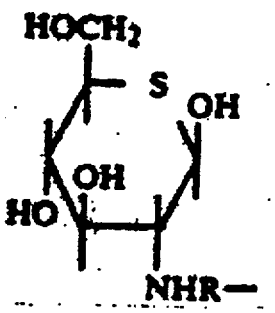

--

UNITED STATES PATENT AND TRADEMARK OFFICE
CERTIFICATE OF CORRECTION

PATENT NO. : 5,055,517
DATED : October 8, 1991
INVENTOR(S) : Robert SHORR et al.

It is certified that error appears in the above-identified patent and that said Letters Patent is hereby corrected as shown below:

Column 22, line 52, delete "wa" and insert therefor "was"

Signed and Sealed this

Twelfth Day of April, 1994

Attest:

Attesting Officer

BRUCE LEHMAN

Commissioner of Patents and Trademarks